(12) United States Patent
Nakaya et al.

(10) Patent No.: US 6,641,538 B2
(45) Date of Patent: Nov. 4, 2003

(54) ULTRASONIC DIAGNOSTIC APPARATUS AND METHOD OF CONTROLLING A ULTRASONIC DIAGNOSTIC APPARATUS

(75) Inventors: Shigemitsu Nakaya, Otawara (JP); Naohisa Kamiyama, Otawara (JP); Huminori Moriyasu, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/295,844

(22) Filed: Nov. 18, 2002

(65) Prior Publication Data

US 2003/0097070 A1 May 22, 2003

(30) Foreign Application Priority Data

Nov. 22, 2001 (JP) ........................................ 2001-358371

(51) Int. Cl.[7] .................................................. A61B 8/00
(52) U.S. Cl. ...................................................... 600/458
(58) Field of Search ........................... 600/458, 437–461

(56) References Cited

U.S. PATENT DOCUMENTS

| | | | |
|---|---|---|---|
| 5,694,937 A | 12/1997 | Kamiyama | |
| 5,735,281 A | 4/1998 | Rafter et al. | |
| 5,833,613 A | * 11/1998 | Averkiou et al. | 600/440 |
| 5,971,928 A | * 10/1999 | Dodd et al. | 600/458 |
| 6,080,107 A | * 6/2000 | Poland | 600/458 |
| 6,104,670 A | * 8/2000 | Hossack et al. | 367/7 |
| 6,108,572 A | * 8/2000 | Panda et al. | 600/407 |
| 6,149,597 A | 11/2000 | Kamiyama | |
| 6,561,982 B2 | * 5/2003 | Greppi et al. | 600/458 |

FOREIGN PATENT DOCUMENTS

WO   WO 01/01865   1/2001

* cited by examiner

Primary Examiner—Francis J. Jaworski
Assistant Examiner—Ruby Jain
(74) Attorney, Agent, or Firm—Oblon, Spivak, McClelland, Maier & Neustadt, P.C.

(57) ABSTRACT

In an ultrasonic diagnostic apparatus, a set of transmitting conditions ML1 optimal for existential diagnosis and two transmitting conditions ML2 and ML3 optimal for qualitative diagnosis are defined for the contrast echo method and selected appropriately according to a sequence of diagnosis for the purpose of gathering and processing ultrasonic images. The transmitting conditions can be switched automatically, from one to the other, or in accordance with a command issued by the operator due to the program registered in advance. A flash transmission is conducted on the transmitting conditions MLh between an existential diagnosis and a qualitative diagnosis. This enables the user to observe the new in-flow of contrast medium into the region being observed.

21 Claims, 7 Drawing Sheets

| Mechanical level | Transmission voltage | Transmission frequency | Transmission frame rate |
|---|---|---|---|
| ML1 | 5V | 3MHz | 10Hz |
| ML2 | 10V | 4MHz | 30Hz |
| ML3 | ,0V | 4MHz | 30Hz |
| ML4 | 30V | 4MHz | 30Hz |
| MLh | 100V | 2MHz | 40Hz |
FIG. 2
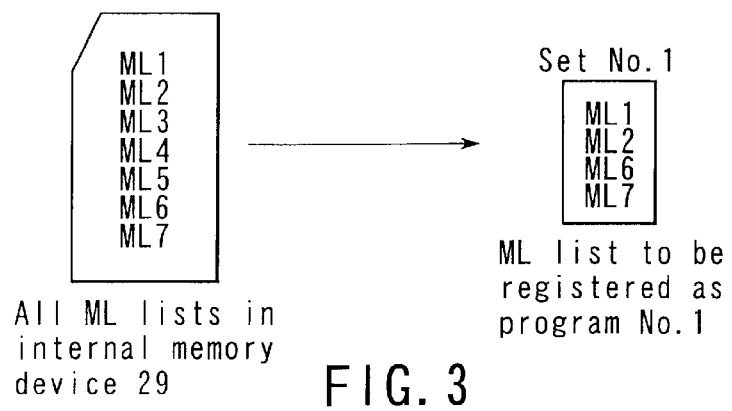
FIG. 3
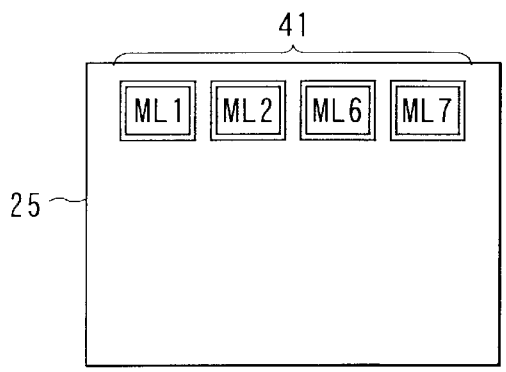
FIG. 4
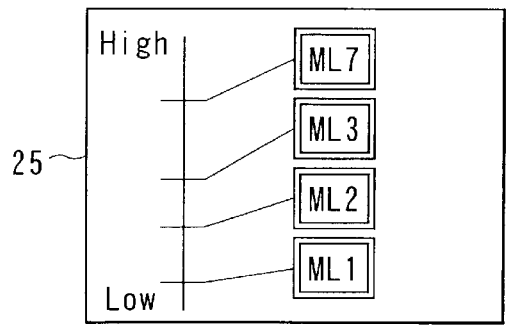
FIG. 5

ULTRASONIC DIAGNOSTIC APPARATUS AND METHOD OF CONTROLLING A ULTRASONIC DIAGNOSTIC APPARATUS

CROSS-REFERENCE TO RELATED APPLICATIONS

This application is based upon and claims the benefit of priority from the prior Japanese Patent Application No. 2001-358371, filed Nov. 22, 2001, the entire contents of which are incorporated herein by reference.

BACKGROUND OF THE INVENTION

1. Field of the Invention

This invention relates to an ultrasonic diagnostic apparatus for use in, for example, medical image diagnoses, and also to a method of controlling such an ultrasonic diagnostic apparatus.

2. Description of the Related Art

Ultrasonic diagnostic apparatuses can display in real time the beating of the heart or the motion of the embryo in the subject, merely by applying an ultrasonic probe to the surface of the subject's body. Furthermore, they can be used repeatedly for the same subject in safety, because they apply no X rays to the subject. Additionally, they are smaller than diagnostic apparatuses of any other type, such as X-ray CT scanners and MRI apparatuses. They can therefore be easily moved to the bedside and can examine the subject. For these and other advantages, ultrasonic diagnostic apparatus are widely used to examine the heart, the abdomen and the urinary organs, in the field of obstetrics and gynecology. Each ultrasonic diagnostic apparatus may have various sizes, depending on what functions the apparatus it performs. Compact ones, small enough to be carried by a single hand, have been developed to date. It is expected that the patient may operate some ultrasonic diagnostic apparatus may be operated by patients in the future.

Various imaging methods are known for ultrasonic image diagnostic apparatus. Among them is a representative one called "contrast echo method." In the contrast echo method, an ultrasonic an contrast medium containing micro-bubbles is injected into the blood vessel of the subject to intensity the scattering ultrasonic echo.

In recent years, ultrasonic contrast media to be injected into the veins have become commercially available. The contrast echo method is now widely employed. In the method, an ultrasonic contrast medium is injected into the vein of the subject to intensity the blood flow signal and to evaluate the dynamic blood flow. This facilitates the examination of the heart or the abdominal organ. In most contrast media, micro-bubbles work as reflectors. The imaging effect of any contrast medium is prominent when it has a high density and is injected in large quantities. It is known, however, that micro-bubbles, which are weak and delicate, collapse when ultrasonic waves are applied to them. Consequently, the time during which the medium remains effective is shortened.

The simplest technique of receiving an echo signal constantly and continuously receiving from such delicate micro-bubbles is to reduce the acoustic pressure of the ultrasonic waves. Generally, as the transmission output decreases in level, the ratio of the level of the received signal to the system noise of the apparatus, or so-called S/N ratio, decreases, rendering it difficult to obtain satisfactory images for diagnosis. The S/N ratio in ultrasonic diagnostic apparatuses has remarkably increased due to the recent advancement in the digital circuit technology. Additionally, it is expected that satisfactorily effective image diagnoses can be achieved in the future at low and intermediate levels of ultrasonic irradiation level. This is because contrast media exhibiting improved resistance to acoustic pressure will be commercially available in the near future.

Typical modes of diagnosis using the contrast echo method include existential diagnosis and qualitative diagnosis. The existential diagnosis is performed by scanning a living organ in three-dimensional fashion and detecting, from the obtained image, a pathologic region, if any, in the organ. To accomplish existential diagnosis, parameters suitable for observing a micro-perfusion image of the organ must be selected and applied to the apparatus. The qualitative diagnosis is to determine the type and progress of disease in the tumor-like lesion detected in a living organ. To achieve qualitative diagnosis, parameters that make the microstructure of the blood vessel more clearly discernible must be selected and applied.

The parameters suitable for existential diagnosis are contradictory to the parameters suitable for qualitative diagnosis. To conduct the two types diagnoses in the single diagnostic sequence by using the conventional ultrasonic diagnostic apparatus, it is necessary to select parameters that are contradictory to one another. Selection of such parameters is very cumbersome and difficult. In other words, to perform both the existential diagnosis and the qualitative diagnosis, the diagnostic sequence must be carried out twice, which requires a long time and much labor. Such a time-consuming, cumbersome operation is a heavy burden to both the operator and the patient.

BRIEF SUMMARY OF THE INVENTION

The present invention has been made in view of the foregoing. An object of the invention is to provide an ultrasonic diagnostic apparatus and a method of controlling such an ultrasonic diagnostic apparatus, which can accomplish both an existential diagnosis and a qualitative diagnosis in a single diagnostic sequence.

The present invention may provide an ultrasonic diagnostic apparatus which comprises: an ultrasonic probe which transmits an ultrasonic wave to a predetermined region of a subject injected a contrast medium and receiving a reflection wave from the subject; a drive signal generation unit configured to generate a drive signal to drive the ultrasonic probe; a controller which controls the drive signal generation unit to switch at least three wave transmitting conditions in a predetermined order, each of the at least three wave transmitting conditions being for acquiring distribution information on the contrast medium applied into the tissues of the predetermined region and showing different contrast medium destructing abilities; and an image generation unit configured to generate an ultrasonic image from the reflection wave obtained by at least one of the ultrasonic waves transmitted respectively in each of the at least three wave transmitting conditions.

The present invention may also provide an ultrasonic diagnostic apparatus which comprises: an ultrasonic probe which transmits an ultrasonic wave to a predetermined region of a subject injected a contrast medium and receives a reflection wave from the subject; a drive signal generation unit configured to generate a drive signal to drive the ultrasonic probe; a controller which controls the drive signal generation unit to switch a first wave transmitting condition which does not destruct the contrast medium substantially, a second wave transmitting condition which substantially destructs the contrast medium and a third wave transmitting condition which differs from the first and second wave transmitting conditions, in a predetermined order; and an image generation unit configured to generate an ultrasonic image on the basis of the reflection wave obtained by at least one of the ultrasonic waves transmitted respectively on each of the first, second and third wave transmitting conditions.

The present invention may provide a method of controlling an ultrasonic diagnostic apparatus which scans a predetermined region of a subject with a contrast medium injected, by using an ultrasonic probe, and which generates an ultrasonic image, the method comprising: supplying drive signals to the ultrasonic probe to switch at least three wave transmitting conditions for acquiring distribution information on the contrast medium in the tissues in the predetermined region, in a predetermined order by the ultrasonic scanning, the at least three wave transmitting conditions showing different contrast medium destructing abilities respectively; and generating an ultrasonic image from the reflection wave obtained from at least one of the ultrasonic waves transmitted respectively in each of the at least three wave transmitting conditions.

The present invention may further provide a memory storing computer-executable program code for controlling an ultrasonic diagnostic apparatus which scans a predetermined region of a subject with a contrast medium injected by using an ultrasonic probe, and which generates an ultrasonic image, the program code comprising: first means for causing a computer to supply drive signals to the ultrasonic probe to switch at least three wave transmitting conditions in a predetermined order, each of the at least three wave transmitting conditions being for acquiring distribution information on the contrast medium in the tissues of the predetermined region and showing different contrast medium destructing abilities; and second means for causing a computer to generate an ultrasonic image from the reflection wave obtained from at least one of the ultrasonic waves transmitted respectively in each of the at least three wave transmitting conditions.

BRIEF DESCRIPTION OF THE SEVERAL VIEWS OF THE DRAWING

FIG. 2 is a list of ultrasonic transmission conditions (transmission voltage, transmission frequency and transmission frame rate) registered in advance in the internal memory device 29 illustrated;

FIG. 3 is a conceptual representation of the program-registering function of MLs;

FIG. 4 illustrates a format of displaying ML buttons 41 to be used for Set No. 1;

FIG. 5 depicts another format of displaying ML buttons 41 to be used for Set No. 1;

DETAILED DESCRIPTION OF THE INVENTION

Figure 1:
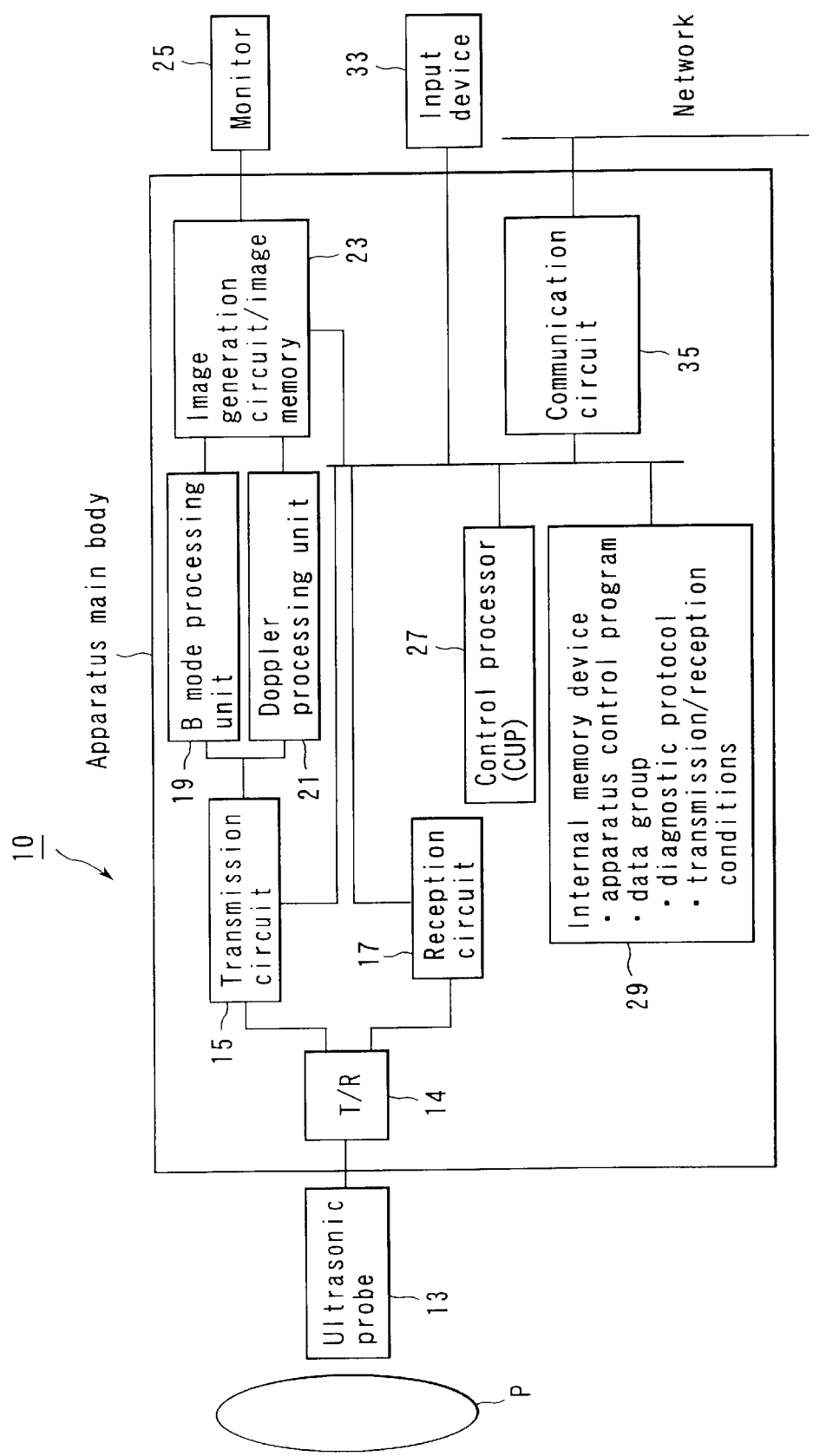
FIG. 1 is a block diagram showing an ultrasonic diagnostic apparatus 10 according to the invention.

The present invention will be described, with reference to the accompanying drawings. The components identical or similar to one another are denoted at the same reference symbols-in the drawings and will not be described repeatedly, unless necessary, in the following description.

FIG. 1 is a block diagram of an ultrasonic diagnostic apparatus 10 according to the invention. First, the configuration of the ultrasonic diagnostic apparatus 10 will be described, with reference to FIG. 1.

The ultrasonic diagnostic apparatus 10 comprises an ultrasonic probe 13, a T/R 14, a transmission circuit 15, a reception circuit 17, a B mode processing system 19, a color Doppler processing system 21, an image generation circuit/image memory 23, a monitor 25, a control processor 27, an internal memory device 29, an input device 33, and a communication device 35.

The ultrasonic probe 13 has piezoelectric vibrators made of piezoelectric ceramic. The vibrators function as acoustic/electric reversible transducers. They are removably connected to the main body of the apparatus 10. The piezoelectric vibrators are juxtaposed and provided at the front end of the probe 13. They are designed to generate an ultrasonic wave from the voltage pulses supplied from the transmission circuit 15.

The T/R 14 is a switch for switching the operation of the ultrasonic probe 13, from transmission to reception or vice versa. More specifically, the transmission circuit 15 supplies a drive signal to the ultrasonic probe 13 when the T/R 14 selects transmitting operation mode. When the T/R 14 selects receiving operation mode, an echo signal received by the ultrasonic probe 13 is transmitted to the reception circuit 17.

The transmission circuit 15 is connected to the probe 13. It has a pulse generator, a transmission delay circuit, and a pulser. The pulse generator repeatedly generates a rate pulse at a rate frequency $f_0$ Hz (period: $1/f_0$ seconds) of, for example, 5 kHz. The rate pulses generated are allotted for transmission channels and transmitted to the transmission delay circuit. The transmission delay circuit delays each rate pulse by a delay time. The delay time is of the value that converges and changes the ultrasonic wave to a beam and determines the transmission directivity. The transmission delay circuit receives a trigger signal, as timing signal, from a trigger signal generator (not shown). The pulser applies a voltage pulse to the probe 13 for each channel when it receives a rate pulse from the transmission delay circuit. Upon receiving a voltage pulse, each piezoelectric vibrator at the front of the ultrasonic probe 13 vibrates, generating an ultrasonic pulse having the center frequency of $f_0$. The ultrasonic pulse is applied to the subject P.

The ultrasonic pulse applied from the ultrasonic probe 13 propagates through the subject P. In the subject P, the ultrasonic pulse is reflected from discontinuous planes of acoustic impedance. The ultrasonic pulse thus reflected returns to the ultrasonic probe 13, in the form of echo. The amplitude of the echo depends on the acoustic impedances of the tissue at the discontinuous plane where the ultrasonic pulse is reflected. The echo generated from the ultrasonic pulse reflected by blood and the surface of any moving cardiac wall depends on the velocity at which the subject P moves in the direction of the beam. The echo undergoes frequency deviation due to the Doppler effect.

In the diagnostic sequence that will be described later, the transmission circuit 15 transmits an ultrasonic wave as a function of the voltage pulse that varies in accordance with various programmed transmission conditions and the transmission frequency. These factors will be described later in detail.

The reception circuit 17 has a pre-amplifier, an A/D converter, a reception delay circuit, and an adder. The pre-amplifier amplifies the echo signal that the reception circuit 17 has received from the probe 13 for each channel. The echo signal amplified has been delayed much enough for the reception delay circuit to determine the reception directivity. The echo signals from the channels are added in the adder to from a signal for one raster. An echo signal (RF signal) is thereby generated. In the echo signal, the reflection component coming in a certain direction that depends on the reception directivity of the received echo signal is emphasized. The reception directivity and the transmission directivity determine the overall directivity (or "scanning line") of ultrasonic transmission/reception.

The B mode processing system 19 has an echo filter, a detection circuit, and an LOG compression circuit, which are not shown. The echo filter is a band-pass filter that is adapted to phase detection in order to extract signals in a desired frequency band. The detection circuit detects the envelope of the echo signal output from the echo filter. It determines a B mode signal for producing a B mode image that visualizes the fundamental wave component for each scanning line in a manner as will be described hereinafter. The LOG compression circuit compresses the B mode detection data by logarithmic transformation.

The color Doppler processing system 21 has a phase detection circuit, an analog/digital converter, an MTI filter, an auto-correlator, and an arithmetic section, which are not shown. The system 21 is configured to extract the blood flow component attributable to the Doppler effect and to acquire blood flow information. The blood flow information includes the average velocity, dispersion and power for a number of points. The blood flow information is sent to the monitor 25 via the image generation circuit/image memory 23. The information is displayed in color in the form of an average velocity image, a dispersion image, a power image and a combined image thereof.

The image generation circuit/image memory 23 receives the string of scanning line signals generated by ultrasonic scans and input from the B mode processing system 19 or the color Doppler processing system 21. The memory 23 transforms the scanning line signals into data of an orthogonal coordinate system, which is based on spatial information. The memory 23 divides the plane obtained from the information on each scanning line after the transformation into pixels. The memory 23 stores information on the reflection intensity of the plane by allocating the pixels to memory addresses. The information is read from the memory 23, as a string of scanning line signals arranged in an ordinary video format that may be that of television. The information thus read is output to the monitor 25 as video signal.

The monitor 25 typically comprises a CRT. It displays a tomographic image represented by the input video signal and showing the tissues of the subject P. More precisely, the monitor displays an image synthesized from a B mode signal, a power signal and a velocity signal, all generated by the image generation circuit/image memory 23.

The control processor 27 controls some of the components of the ultrasonic diagnostic apparatus 10; it functions as control center.

The internal memory device 29 stores a control program and image data necessary for collecting, processing and displaying ordinary ultrasonic images. The internal memory device 29 also stores a control program necessary for realizing transmission conditions for observing perfusion images and transmission conditions for making the microstructure of blood vessel more discernible in a diagnostic sequence, and ultrasonic transmission conditions that can be used for ultrasonic transmissions according to the program. Ultrasonic transmission conditions are parameters that influence the physical conditions of the ultrasonic wave to be transmitted including the acoustic pressure to be transmitted into the living body, the transmission frequency, the number of waves to be transmitted, the number of times of emissions per unit time of a transmission pulse and so on. The ultrasonic transmission conditions are stored in the internal memory device 29 as default conditions. The operator can alter these conditions and register other conditions, by operating the input device 33 in a predetermined manner.

FIG. 2 is a list of ultrasonic transmission conditions (transmission voltage, transmission frequency and transmission frame rate) registered in advance in an internal memory device 29. The abbreviation "ML" used in FIG. 2 and in the following description stands for a mechanical level. A mechanical level is a comprehensive ultrasonic transmission condition defined by the three parameters of transmission voltage, transmission frequency and transmission frame rate. Thus, any ML selected means that a transmission voltage, a transmission frequency and a transmission frame rate are uniquely defined.

As FIG. 2 shows, at ML1, a transmission condition that provides a low contrast medium destructing ability is defined for observation of a perfusion image (low acoustic pressure level). At ML2 through ML5, contrast medium destructing abilities higher than the one defined for observation of a perfusion image are provided and arranged in the ascending order. These levels provide medium contrast medium destructing abilities for observation of a vascular image (between the destruction ability for observation of a perfusion image and the one for flash echo) (middle to high acoustic pressure levels). At MLh, very high transmission conditions are defined for purpose of destructing microbubbles on the scanning plane in a short period of time (so as to be used for the flash echo method) (high acoustic level).

ML is also used as index for the degree of ability of destructing contrast media. In this embodiment, the number affixed to ML shows a level of ability of destructing contrast media. That is, ML2 in FIG. 2 represents an ability of destructing contrast media higher than ML1. If two MLs represent the same transmission voltage and the same transmission frequency and represent different transmission frame rates, one ML that represents the higher transmission frame rate is affixed with a larger number. This is because, when two ultrasonic waves transmitted with a same acoustic pressure, the ML showing the higher transmission rate can destruct the contrast medium within unit time.

The ultrasonic diagnostic apparatus 10 can register any combination of MLs in advance as a program. When this program is selected, a diagnostic sequence that uses only the MLs of the program is carried out, as will be described in greater detail hereinafter.

The ML most suited for a diagnostic image can be determined when the physical properties of the contrast medium are known. In view of this, it is desired that the ultrasonic diagnostic apparatus 10 have a number of MLs as default values. As FIG. 2 shows, a combination of five MLs is defined. Nonetheless, more than five MLs can be stored.

The ultrasonic diagnostic apparatus 10 will be further described, with reference to FIG. 1. The input device 33 is an interface (including a mouse or track ball, a mode changeover switch and a keyboard), a TCS (Touch Command Screen), or the like, which operator uses to define a region of interest (ROI) in order to input various commands, instructions and data.

(Existential Diagnosis, Qualitative Diagnosis)

The ultrasonic diagnostic apparatus 10 of the configuration described above is used to observe the dynamic blood flow by performing the contrast echo method that uses an ultrasonic contrast medium for the purpose of diagnosing the subject. Typical modes of diagnosis of the organs, such as the liver, the pancreas and the spleen, in which tumor-like lesions (occupying diseases) may develop, include existential diagnosis and qualitative diagnosis. These diagnoses will be described below.

Existential diagnosis is a diagnosis mode of detecting a morbid region (tumor-like lesion) in living organs by scanning the organs three-dimensionally. In some cases, tumor-like lesions can be detected by using an ordinary B mode tomographic image. In most cases, however, the doctor needs to scrutinize the image to detect tumor-like lesions. This is inevitably because the morbid region and the normal tissues do not show any difference in terms of luminance contrast of image. Hence, the morbid region and the normal tissue can hardly be distinguished from each other. Particularly, small morbid regions and regions with unclear lesion boundaries may be overlooked frequently.

Generally, the image of such a tumor-like lesion seen after a contrast medium is applied looks quite different from the image seen before the contrast medium is applied. Normal tissues provides an image with a relatively homogeneous rise of luminance due to perfusion of blood, and the dynamic blood flow of a tumor clearly differs from that of normal tissues. Thus, the image of a tumor is clearly detected from the luminance contrast ratio of the image. Therefore, a perfusion image of tissues is preferably used for existential diagnosis. A perfusion image of tissues can be obtained by processing the information on a very slow blood flow.

To acquire information on a very slow blood flow, the apparatus may need to (1) minimize the transmitted acoustic pressure in order to reduce the loss of micro-bubbles, (2) to maximize the time intervals of ultrasonic irradiation in order not to break micro-bubbles (so-called intermittent transmission method), or (3) to detect only higher harmonic signal components (so-called harmonic imaging method). In most cases, the method (1) is used to extracting a perfusion image of tissues for the purpose of existential diagnosis as described for this embodiment. It is desirable to define parameters that are suited for observing an image of micro perfusion of an organ, or so-called a perfusion image, for the ultrasonic diagnostic apparatus.

Qualitative diagnosis, on the other hand, is a mode of diagnosing the type and progress of disease in the detected tumor-like lesion. One of its principal functions is to discriminate malignant tumor (primary liver cancer) and benign tumor (hemangioma). The qualitative diagnosis can be utilized in the treatment of a detected primary liver cancer, by observing how richly blood vessels are formed in the inside of the tumor.

Thus, it is important to know more details a lesion through qualitative diagnosis. To perform successful qualitative diagnosis, it is essential to determine the blood vessel structure from the blood flow in blood vessels, which is faster than perfusion, though the structure may be very fine. If parameters similar to those applied to existential diagnosis are selected for qualitative diagnosis, the microstructure of blood vessels will be hidden behind the luminance of perfusion. This will render it difficult to observe the object of diagnosis. This can be avoided by (1') appropriately raising the acoustic pressure to be transmitted to detect only blood flows of the vascular system showing a relatively high supply rate so as not to detect slow blood flows of the perfusion level, (2') intermittently transmitting acoustic pressure at intervals good for detecting only blood flows showing a relatively high supply rate, or (3') using not only harmonic signals but also an imaging method for detecting the flow rate (such as Doppler method).

When the measure (1') is taken, it is no longer possible to observe the micro structure of blood vessels and the perfusion image respectively on the conditions of ultrasonic diagnosis that are suited for existential diagnosis and on the conditions of ultrasonic diagnosis that are suited for qualitative diagnosis. This is because it is desirable to define parameters for the diagnostic apparatus that make the microstructure of blood vessels clearly discernible for qualitative diagnosis.

With the ultrasonic diagnostic apparatus 10, the conditions of ultrasonic diagnosis suited for existential diagnosis and those suited for qualitative diagnosis, e.g., the conditions for transmitting an ultrasonic wave, can be quickly and easily switched so that the both diagnoses can be conducted in a single diagnostic sequence. This will be more clearly understood from the technique of collecting and displaying ultrasonic images, which will be described later.

(Program Registration of MLs)

Now, the program feature of MLs, which the ultrasonic diagnostic apparatus 10 has, will be described. This feature is used to register any combinations of MLs as programs in advance. When a program is selected, a diagnostic sequence that uses only the MLs of this program is executed.

FIG. 3 illustrates a program registering feature for MLs. Assume that seven mechanical effects of ML1 to ML7 are registered in the internal memory device 29 in advance as shown in FIG. 3. Then, an ML list containing ML1, ML2, ML6 and ML7 is registered as program Set No. 1.

To execute the registered program Set No. 1 to carry out a diagnostic sequence, only the MLs of the program Set No. 1 can be used. More specifically, when the operator executing the diagnostic sequence requests "Set No. 1", the buttons 41 of MLs of Set No. 1 are displayed on the TCS or the monitor 25 of the apparatus 10 as is illustrated in FIG. 4.

Thus, the operator can use only the MLs of Set No. 1 that correspond to the displayed buttons 41. The operator can therefore quickly and easily determine the conditions of ultrasonic transmission that are suited for any of various diagnostic images including a perfusion image and a vascular image by selecting one of the ML buttons.

The mode of displaying ML buttons 41 is not limited to the one shown in FIG. 4. Rather, it is possible to use various display modes. For example, MLs may be automatically arranged in the ascending order (or the descending order) of the actual values of the MLs (mechanical effects), whereas those shown in FIG. 4 are arranged in the ascending order of the numbers affixed to them. The display mode shown in FIG. 5, where the values of MLs are more visually and quantitatively shown, may preferably be used.

Figure 6:
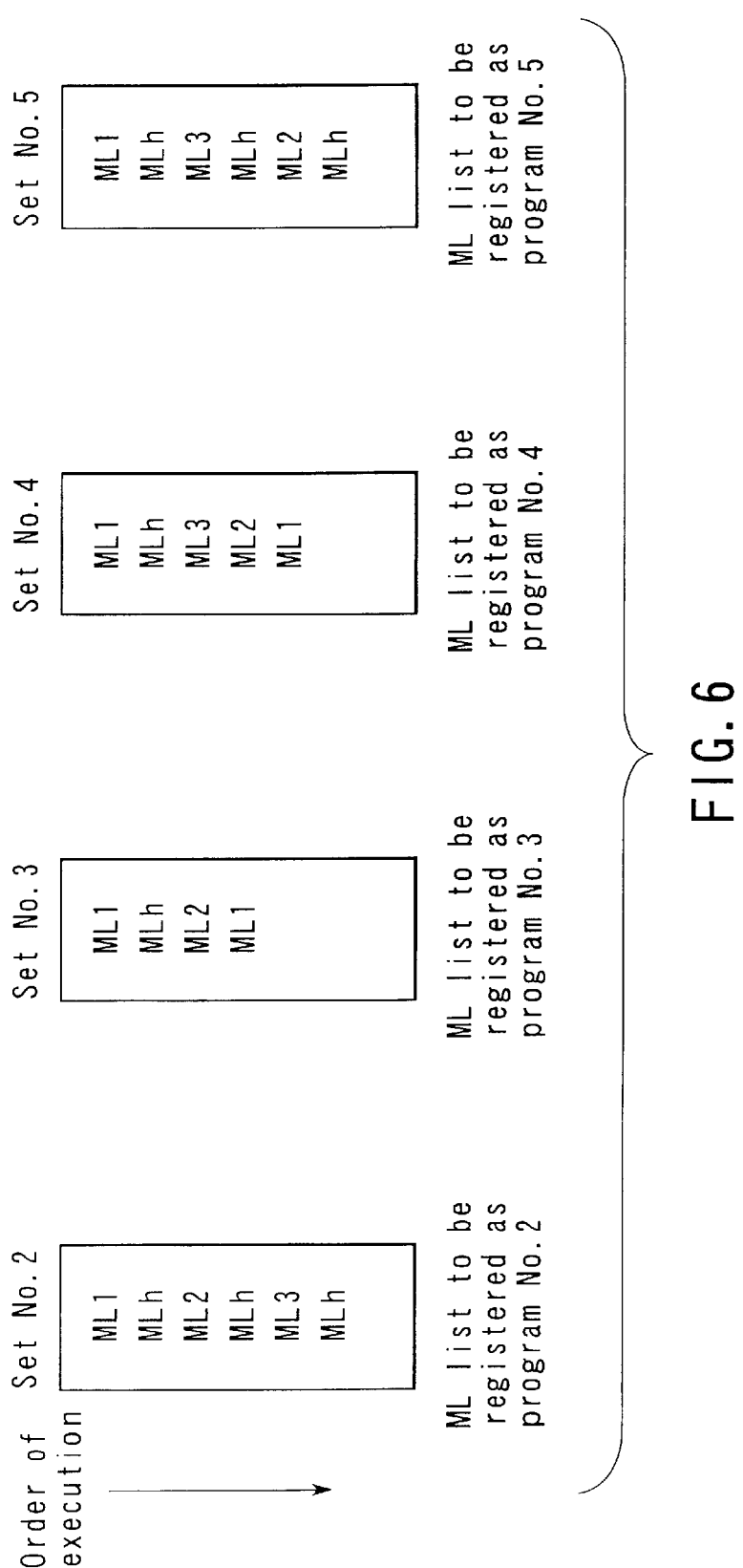
FIG. 6 is a conceptual illustration of a program-registering function of MLs, which is different from the function shown in FIG. 3.

Program registration of MLs is not limited to the instance of FIG. 3. Sets of selected values of MLs may be registered in the order of execution (selection) as shown in FIG. 6. For example, the conditions MLh is inserted between ML1 and ML2 and between ML2 and ML3 without fail in Set No. 2 and the sequence is registered as part of the program.

The use of a single button is sufficient to request Set No. 2 of FIG. 6 to shift MLs. The operator only needs to push the button repeatedly to shift the MLs until a desired set of conditions is selected.

Preferably, a button for skipping MLs is provided to get to the desired ML quickly. Likewise, a "reset" button for returning to the head of the sequence is preferably provided.

It is desired that individual "attributes" can be registered for the registered sets of conditions. The term of "attributes" used herein means information other than the transmission voltage, the transmission frequency and the transmission frame rate. For instance, an attribute may provide a condition that a shift from a particular ML to a next ML requires an input by pushing a specific button. Another attribute may provide a condition that a specific execution time needs to be defined. For example, the ultrasonic transmission may be carried out at MLh only for T seconds and then the next set of conditions is automatically selected.

(Collecting and Displaying Ultrasonic Images)

How the ultrasonic diagnostic apparatus 10 performs a diagnostic sequence of collecting perfusion images for existential diagnosis and vascular images for achieve qualitative diagnosis will be described, with reference to FIGS. 7A through 12.

Figure 7A:
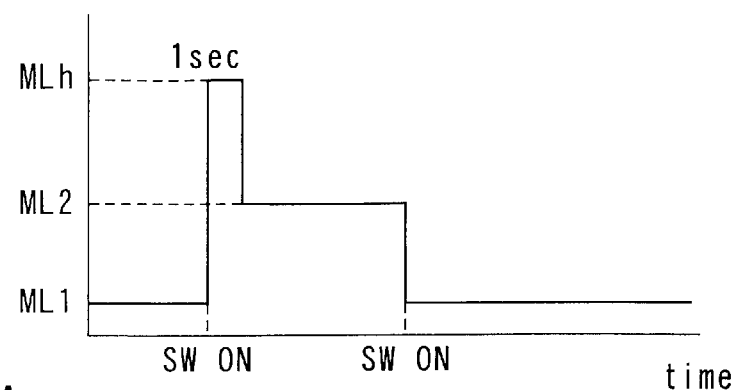
FIG. 7A shows the sequence of operation of ultrasonic transmission, which is performed when Set No. 3 in FIG. 6 is used.
Figure 7B:
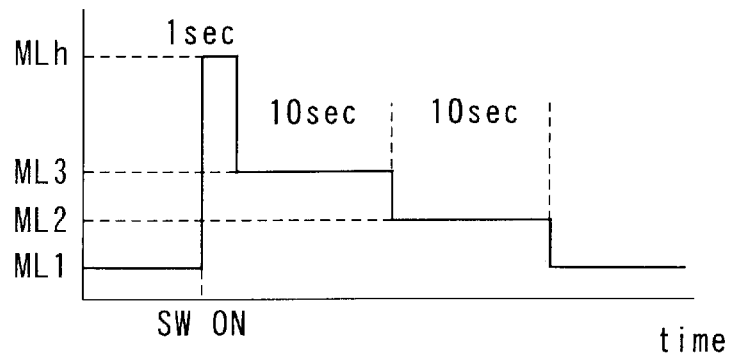
FIG. 7B illustrates the sequence of operation of ultrasonic transmission, which is performed when Set No. 4 in FIG. 6 is used.
Figure 7C:
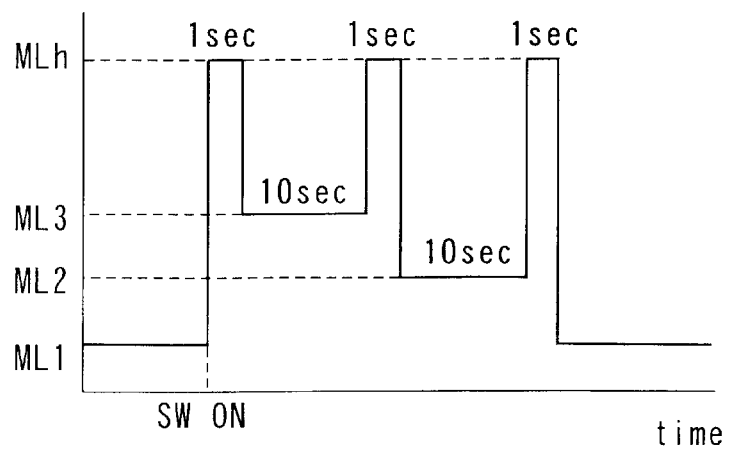
FIG. 7C depicts the sequence of operation of ultrasonic transmission, which is performed when Set No. 5 in FIG. 6 is used.
Figure 8:
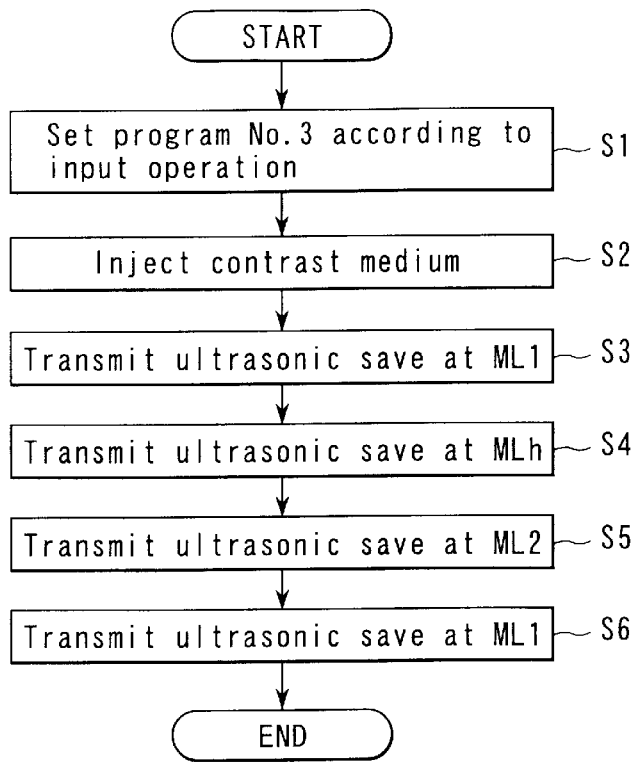
FIG. 8 is a flowchart showing the sequence of ultrasonic diagnosis, which is carried out when Set No. 3 in FIG. 6 is used.
Figure 9:
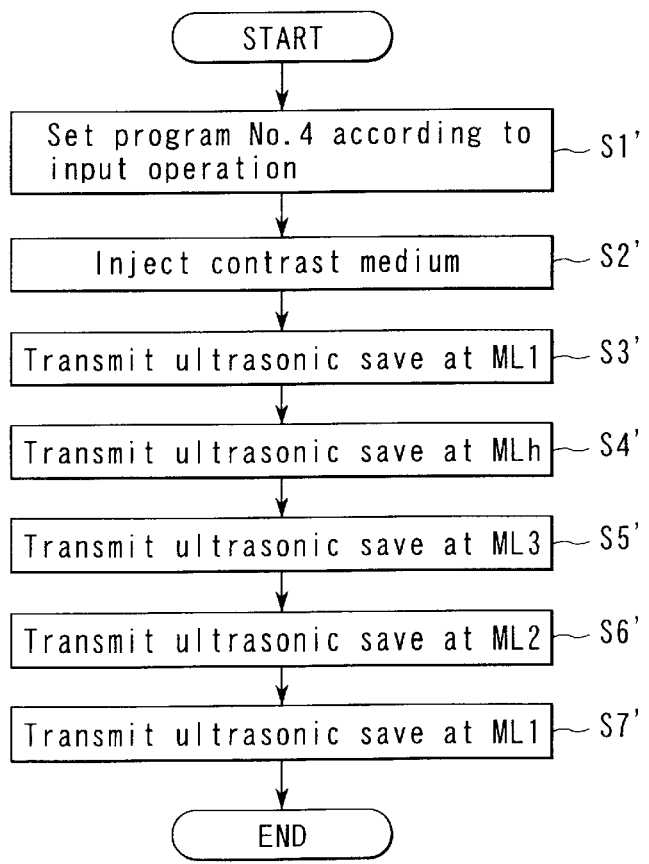
FIG. 9 is a flowchart illustrating the sequence of ultrasonic diagnosis, which is performed when Set No. 4 in FIG. 6 is used.
Figure 10:
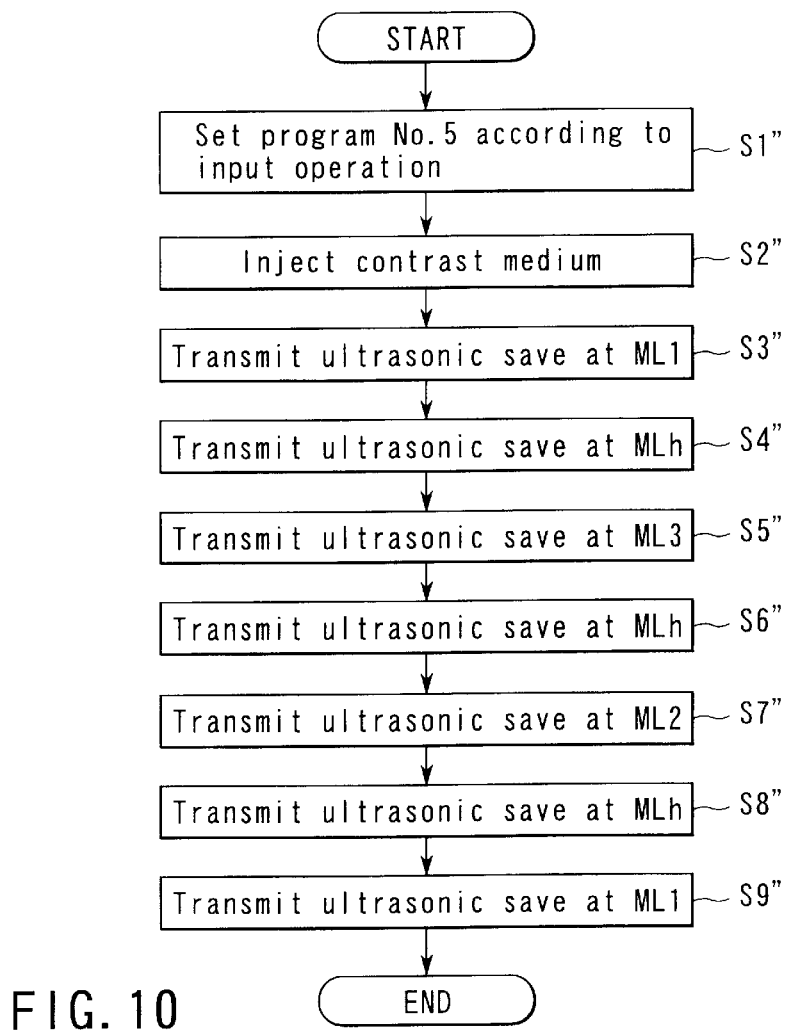
FIG. 10 is a flowchart showing the sequence of ultrasonic diagnosis, which is performed when Set No. 5 in FIG. 6 is used.

FIGS. 7A, 7B and 7C illustrate the sequences of ultrasonic transmission when the programs of Set No. 3, Set No. 4 and Set No. 5 of FIG. 6 are respectively used. FIGS. 8, 9 and 10 are flowcharts explaining the sequences of ultrasonic diagnosis that is performed when the programs of Set No. 3, Set No. 4 and Set No. 5 of FIG. 6 are respectively used.

First, the sequence of ultrasonic diagnosis performed by using the program Set No. 3 will be explained with reference to FIGS. 7A and 8.

As FIG. 8 depicts, the Set No. 3 is read out from the internal memory device 29 and stored in the working memory of the control processor 27 when the operator selects the program Set No. 3 by carrying out a predetermined input operation (Step S1).

When Set No. 3 is thus selected, a contrast medium is injected (Step S2). An ultrasonic wave is transmitted according to the registered program. "SonoVue (BRI)" may be a non-limitative example of preferable contrast medium that can be injected in Step S2. Other preferable examples of contrast medium "Levovist, Optison, Sonozoid" or the like can be used.

Then, an ultrasonic wave is transmitted in the conditions of ML1 that are suitable for collecting perfusion images of tissues for the purpose of existential diagnosis and moving perfusion images are collected and displayed (Step S3).

Once the ultrasonic wave has been transmitted in the conditions of ML1, it is possible to observe the alignment of the region to be diagnosed, the new in-flow of the contrast medium, and a perfusion image showing the contrast medium pervading the entire tissues on a real time basis. The transmission voltage of ML1 can be shifted sequentially by operating the volume control arranged on the ultrasonic diagnostic apparatus for the purpose of regulating the transmission gain.

A command for a switch of ML is input when the operator pushes a predetermined button for shifting the conditions. The conditions of MLh are thereby selected. Then, an ultrasonic wave is transmitted in the conditions of MLh to destruct the bubbles of the contrast medium in the region being observed (Step S4). It is now possible to observe the new in-flow of the contrast medium into the region being observed for the purpose of diagnosis in the next step. Note that, the attribute of MLh is defined to be "1 second" as seen from FIG. 7A. Therefore, the conditions of transmission are switched to those of ML2 that are automatically selected after one second.

Subsequently, an ultrasonic wave is transmitted in the conditions of ML2 that are suitable for observing blood flows of the vascular system showing a relatively high supply rate for the purpose of qualitative diagnosis and moving vascular images are collected and displayed on a real time basis (Step S5). As a result, the contrast medium gradually flowing into blood vessels and the gradual rise of luminance in blood vessels can be observed.

When the operator pushes again the switch for shifting the conditions of transmission, an ultrasonic wave is transmitted on the conditions of ML1 again. A moving ultrasonic image is displayed in real time. At this time, the interior of any blood vessel that has a high flow rate is displayed at a high luminance level (Step S6). This is because the contrast medium is made to flow in to show a high concentration level, while tissues are so displayed as to visualize the increasing luminance.

The ultrasonic images are thus collected and displayed in the conditions of Set No. 3. This diagnostic sequence may be repeated until a command for terminating the diagnostic sequence is input typically by way of a button. Preferably, an operation of ultrasonic transmission/reception, e.g., an operation of collecting images in a B mode, is conducted after the diagnostic sequence on the conditions of Set No. 3 is completed and before the diagnostic sequence on the conditions of Set No. 3 is started.

How the sequence of ultrasonic diagnosis is performed when the program Set No. 4 is used will be described, with reference to FIGS. 7B and 9.

As FIG. 9 illustrates, the Set No. 4 is read out from the internal memory device 29 and stored into the working memory of the control processor 27 when the operator selects the program Set No. 4 by carrying out a predetermined input operation (Step S1').

Step S2' through Step S4' identical to Step S2 through Step S4 shown in FIG. 8 are carried out.

Subsequently, an ultrasonic wave is transmitted in the conditions of ML3 that are suitable for observing blood flows of the vascular system showing a relatively high supply rate for the purpose of qualitative diagnosis and moving vascular images are collected (Step S5'). As a result, it is possible to observe the contrast medium gradually flowing into blood vessels and the gradual rise of luminance in blood vessels on a real time basis. Note that, as shown in FIG. 7B, the attribute of ML3 is defined to be "10 second" for Set No. 4. Therefore, the conditions of transmission are switched to those of ML2 that are automatically selected after ten second.

Thereafter, an ultrasonic wave is transmitted in the conditions of ML2, which is lower than ML3 for the purpose of qualitative diagnosis, and moving vascular images are collected and displayed (Step S6'). As a result, it is possible to observe moving vascular images suitably depicting a finer vascular system. The moving vascular images have a lower flow rate than images obtained at ML3 in real time. Since ML2 and ML3 are different in terms of ability of destructing contrast media, moving ultrasonic images that show different changing rates of luminance can be observed as the contrast medium is made to flow through blood vessels. The ability of destructing contrast media is lower at ML2 than at ML3. The changing rate of luminance in blood vessels is therefore higher at ML2 than at ML3. Thus, the contrast medium can be observed satisfactorily because ML2 and ML3 provide moving ultrasonic images with different changing rates of luminance. In this embodiment, the attribute of ML2 is also defined to be "10 second" for Set No. 4. Hence, the conditions of transmission are switched to those of ML1 that are automatically selected after ten second.

Then, an ultrasonic wave is transmitted in the conditions of ML1 once again, and a moving perfusion image of tissues is displayed for observation on a real time basis (Step S7').

Thus, the ultrasonic images are collected and displayed in the conditions of Set No. 4. Preferably, an operation of ultrasonic transmission/reception, e.g., an operation of collecting images in a B mode, is conducted as described above, after the completion of the diagnostic sequence on the conditions of Set No. 4 and before the start of the diagnostic sequence on the conditions of Set No. 4.

The sequence of operation of ultrasonic diagnosis is performed when the program Set No. 5, as will be described with reference to FIGS. 7C and 10. In this diagnostic sequence, a flash transmission of 1 second on the conditions of MLh is inserted at the time of switching from an ultrasonic transmission for existential diagnosis to an ultrasonic transmission for qualitative diagnosis. As a result, the contrast medium in the region being observed can be wiped out and a new in-flow of contrast medium into the region of observation can be observed.

As shown in FIG. 10, as the operator selects the program Set No. 5 by carrying out a predetermined input operation, the Set No. 5 is read out from the internal memory device 29 and stored in the working memory of the control processor 27 (Step S1").

Then, the operations of Step S2" through Step S4" are carried out as in the case of Step S2 through Step S4 in FIG. 8 (Step S2" through 4").

Subsequently, an ultrasonic wave is actually transmitted on the conditions of ML3 that are suitable for observing blood flows of the vascular system showing a relatively high supply rate for the purpose of qualitative diagnosis and moving vascular images are collected and displayed (Step S5"). As a result of the ultrasonic transmission on the conditions of ML3, it is possible to observe the contrast medium gradually flowing into blood vessels by moving vascular images on a real time basis. Note that the attribute of ML3 is defined to be "10 second". Therefore, the conditions of transmission are switched to those of MLh that are automatically selected after ten second.

Thereafter, a flash transmission is conducted on the conditions of MHh in the 10 seconds of Step S5" for the purpose of destructing the accumulated contrast medium (Step S6"). This ultrasonic transmission in the conditions of MLh is conducted for 1 second as in the case of Step S4" and the conditions of transmission are switched to those of ML2 that are automatically selected.

Then, an ultrasonic wave is transmitted in the conditions of ML2, which is lower than ML3 for the purpose of qualitative diagnosis, and moving vascular images are collected and displayed (Step S7"). As a result, moving vascular images suitably depicting a finer vascular system that has a lower flow rate than images obtained at ML3 can be observed in real time. The attribute of ML2 is also defined to be "10 second" as shown in FIG. 7C. Hence, the conditions of transmission are switched to those of MLh that are automatically selected after ten second.

Thereafter, a flash transmission is conducted for one second for the purpose of destructing the contrast medium accumulated for 10 seconds at Step S7" (Step S8"). Subsequently, the conditions of transmission are switched to those of ML1 that are automatically selected.

Then, an ultrasonic wave is transmitted in the conditions of ML1 so that a perfusion image of tissues where the contrast medium is being accumulated can be observed in real time (Step S9").

The ultrasonic images are collected and displayed in the conditions of Set No. 5 by performing the above sequence. Preferably, an operation of ultrasonic transmission/reception, e.g., an operation of collecting images in a B mode, is conducted after the completion of the diagnostic sequence on the conditions of Set No. 5.

During the sequence of existential diagnosis and the sequence of qualitative diagnosis, a moving perfusion image and/or a moving vascular image can be displayed on the monitor 25 in a manner as described below.

Figure 11:
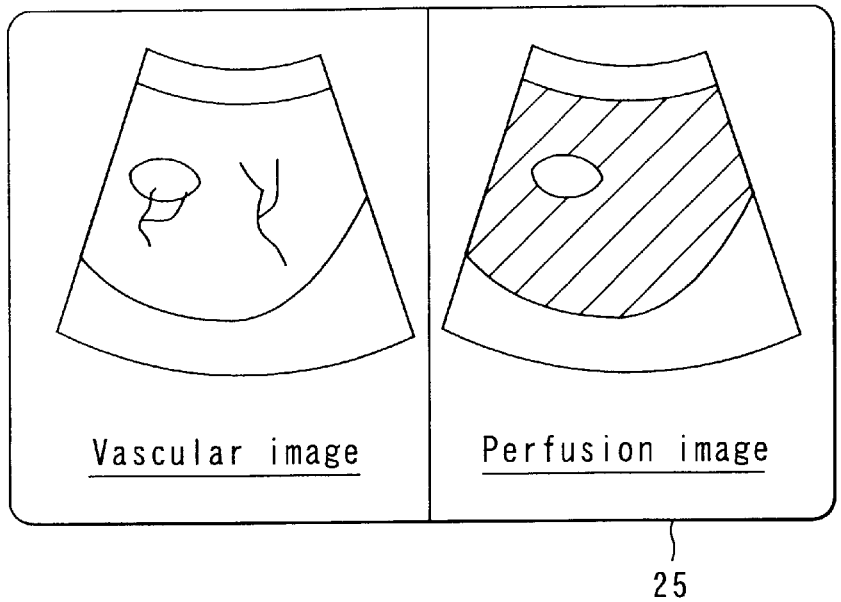
FIG. 11 shows a perfusion image and a vascular image that are displayed side by side, on the monitor 25.

FIG. 11 shows a moving perfusion image and a moving vascular image, which are displayed, in juxtaposition on a monitor 25. As seen form FIG. 11, the display screen of the monitor 25 is divided into two parts allocated respectively to a perfusion image and a vascular image in order to display them simultaneously.

In the display mode of FIG. 11, the most updated image can be automatically displayed as perfusion image selected or as vascular image selected, by defining an attribute for judging "which sets of conditions are selected with priority" for transmission. More specifically, in a diagnostic sequence, a perfusion image is displayed (a moving perfusion image is displayed on a real time basis) if the attribute assigned to the conditions of transmission of ML is for observing a perfusion image. If the assigned attribute is for observing a vascular image, a vascular image is displayed. In an ordinary ultrasonic diagnosis system, the most recently collected image is held on the screen as the image that is not active. The operator can therefore see a perfusion image and a vascular image on the same display screen simultaneously.

Figure 12:
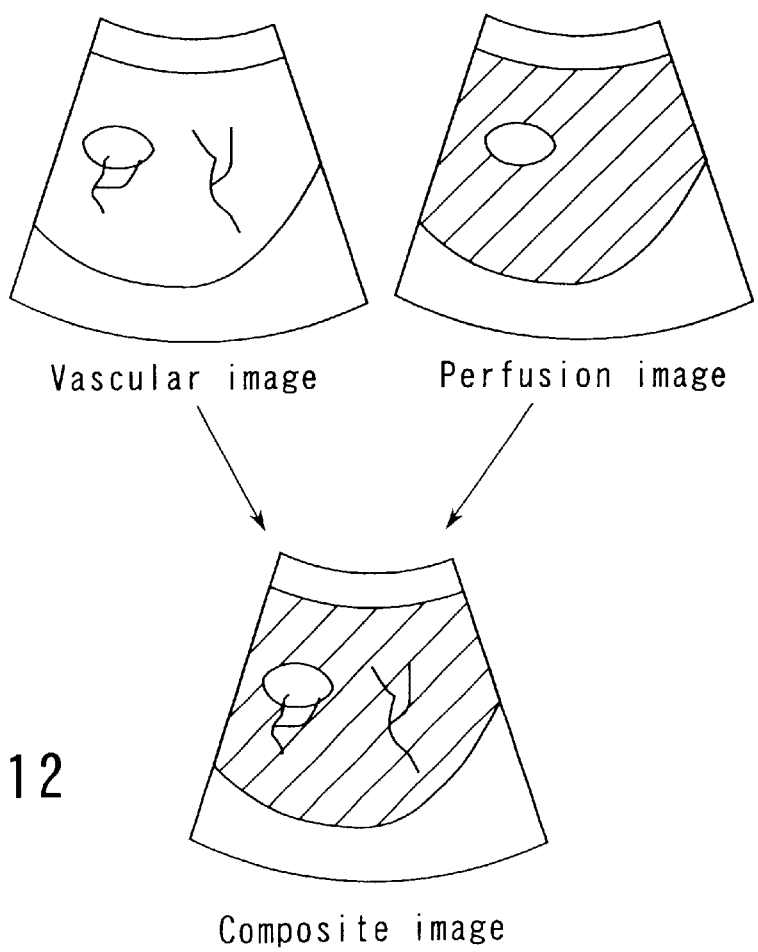
FIG. 12 shows a synthetically combined image consisting of a perfusion image and a vascular image that overlap each other, with their spatial postures corresponding to each other.

An synthetically combined image can be displayed, which consists of a perfusion image and a vascular image that have same spatial posture and overlap each other as is illustrated in FIG. 12. To enable the operator to distinguish the two images without fail, it is preferred that the perfusion image and the vascular image be displayed in different colors with different hue scales. If the images are so displayed, blood flows in blood vessels can be structurally clearly observed in an echo image of tissues containing perfusion for the ease of diagnosis.

The present invention provides the following advantages.

Figure 13:
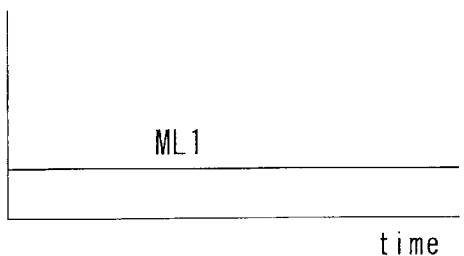
FIG. 13 is a diagram explaining the effect of an ultrasonic diagnostic apparatus according to the invention.
Figure 14:
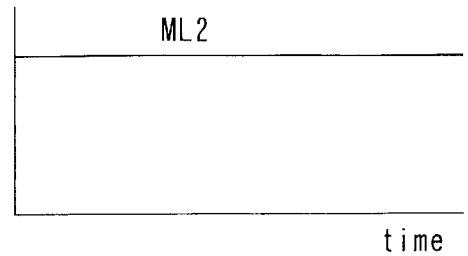
FIG. 14 is a diagram explaining the effect of an ultrasonic diagnostic apparatus according to the invention.

As described above, an ultrasonic wave must be transmitted at a low ML to reduce the loss of micro-bubbles as shown in FIG. 13, thereby to obtain a perfusion image of tissues for existential diagnosis. To perform qualitative diagnosis, the operator must select a relatively high ML to detect only blood flows in the vascular system, which shows a relatively high supply rate, and to obtain a vascular image. With the conventional ultrasonic diagnostic apparatuses it is impossible to obtain the two images simultaneously. Therefore, the operator of any conventional apparatus must select a desired condition by turning, for example, the dial for adjusting the acoustic pressure of the ultrasonic wave that is to be transmitted. However, the acoustic pressure of the ultrasonic wave is not the sole parameter for defining ML. Consequently, the operator needs to operate the frequency button and other buttons at the same time he or she rotates of the dial.

With the ultrasonic diagnostic apparatus according to the invention, optimal transmission conditions for both existential diagnosis and qualitative diagnosis can be selected in the contrast echo method. In addition, ultrasonic images are collected and processed according to the diagnostic sequence provided for the two types of diagnosis that are appropriately switched. Conditions of ultrasonic transmission are selected in accordance with the program registered in advance, either automatically or as the operator pushes a button, thus generating a command for selection of conditions. Therefore, both the protocol for existential diagnosis and the protocol for qualitative diagnosis can be followed quickly and easily in a single diagnostic sequence, though their optimal conditions of transmission contradict each other. As a result, an occupying disease (tumor) can be detected by means of the protocol for existential diagnosis and can be identified by means of the protocol for qualitative diagnosis.

Additionally, ultrasonic images can be collected by using a high luminance echo signal and the new in-flow of contrast medium into the region of interest can be observed in the next existential diagnosis or qualitative diagnosis, by effecting a flash transmission between an existential diagnosis and a qualitative diagnosis.

The ultrasonic diagnostic apparatus according to the invention can register a desired combination of MLs as a program. Therefore, the operator can determine a desired sequence, and existential diagnosis and qualitative diagnosis can be conducted easily and quickly in accordance with the sequence.

The perfusion image and the vascular image collected in a diagnostic sequence including existential diagnosis and qualitative diagnosis are displayed side by side or overlap each other. Thus, the observer can compare the perfusion image and the vascular image more easily than otherwise.

As has been described, the present invention provides an ultrasonic diagnostic apparatus that can display a diagnostic sequence including both existential diagnosis and qualitative diagnosis, and provide a method of controlling such an ultrasonic diagnostic apparatus.

What is claimed is:

1. An ultrasonic diagnostic apparatus comprising:
   an ultrasonic probe which transmits an ultrasonic wave to a predetermined region of a subject injected with a contrast medium and receiving a reflection wave from the subject;
   a drive signal generation unit configured to generate a drive signal to drive said ultrasonic probe;
   a controller which controls said drive signal generation unit to switch at least three wave transmitting conditions in a predetermined order, each of the at least three wave transmitting conditions being for acquiring distribution information on the contrast medium applied into tissues of said predetermined region and showing different contrast medium destructing abilities; and
   an image generation unit configured to generate an ultrasonic image from the reflection wave obtained by at least one of the ultrasonic waves transmitted respectively in each of the at least three wave transmitting conditions.

2. The ultrasonic diagnostic apparatus according to claim 1, wherein the at least three wave transmitting conditions include the first wave transmitting condition for acquiring ultrasonic image without destructing the contrast medium, the second wave transmitting condition for destructing the contrast medium and the third wave transmitting condition different from the first and second wave transmitting conditions; said controller controls said drive signal generation unit to switch the second, third and first wave transmitting conditions sequentially; and
   said image generation unit generates in real time a plurality of ultrasonic images from the reflection wave obtained by an ultrasonic wave transmitted in the third wave transmitting condition and generates in real time a plurality of ultrasonic images from the reflection wave obtained by an ultrasonic wave transmitted in the first wave transmitting condition.

3. The ultrasonic diagnostic apparatus according to claim 1, wherein each of the at least three wave transmitting conditions includes at least one item selected from a group consisting of an acoustic pressure, a voltage of the drive signal to drive said ultrasonic probe, an ultrasonic frequency, number of ultrasonic waves and a number of the drive signals generated per unit time.

4. The ultrasonic diagnostic apparatus according to claim 1, further comprising: a memory which stores a first program defining a predetermined sequence of diagnosis in such a manner to switch the first wave transmitting condition, the second wave transmitting condition and the third wave transmitting condition in a predetermined order to diagnose blood flow in tissues and the blood flow in a vascular system;
   wherein said controller controls said drive signal generation unit according to the first program.

5. The ultrasonic diagnostic apparatus according to claim 1, further comprising: a program registration unit configured to register newly a second program different from the first program;
   wherein said memory stores the second program; and
   said controller controls said drive signal generation unit according to the first program or the second program.

6. The ultrasonic diagnostic apparatus according to claim 1, further comprising: an input device to input a command for switching the at least three wave transmitting conditions.

7. The ultrasonic diagnostic apparatus according to claim 1, wherein timings of the switching the at least three wave transmitting conditions can be set arbitrary; and said controller controls said drive signal generation unit to switch the at least three wave transmitting conditions automatically at preset timing.

8. The ultrasonic diagnostic apparatus according to claim 1, further comprising: a display device which displays a first ultrasonic image and a second ultrasonic image simultaneously, either separated from each other or overlapping each other at spatial positions, the first ultrasonic image being obtained from the ultrasonic wave transmitted in the first wave transmitting condition and the second ultrasonic image being obtained from the ultrasonic wave transmitted in the third wave transmitting conditions.

9. An ultrasonic diagnostic apparatus comprising:

an ultrasonic probe which transmits an ultrasonic wave to a predetermined region of a subject injected with a contrast medium and receives a reflection wave from the subject;

a drive signal generation unit configured to generate a drive signal to drive said ultrasonic probe;

a controller which controls said drive signal generation unit to switch a first wave transmitting condition which does not destruct the contrast medium, a second wave transmitting condition which destructs the contrast medium and a third wave transmitting condition which differs from the first and second wave transmitting conditions, in a predetermined order; and an image generation unit configured to generate an ultrasonic image on the basis of the reflection wave obtained by at least one of the ultrasonic waves transmitted respectively on each of the first, second and third wave transmitting conditions.

10. The ultrasonic diagnostic apparatus according to claim 9, wherein said controller controls said drive signal generation unit to switch the first wave transmitting conditions, the second wave transmitting conditions, the third wave transmitting conditions and a fourth wave transmitting conditions which differs from the first, second and third wave transmitting conditions in a predetermined order.

11. A method of controlling an ultrasonic diagnostic apparatus which scans a predetermined region of a subject with a contrast medium injected, by using an ultrasonic probe, and which generates an ultrasonic image, said method comprising:

supplying drive signals to said ultrasonic probe to switch at least three wave transmitting conditions for acquiring distribution information on the contrast medium in tissues in said predetermined region, in a predetermined order by said ultrasonic scanning, the at least three wave transmitting conditions showing different contrast medium destructing abilities respectively; and generating an ultrasonic image from a reflection wave obtained from at least one of the ultrasonic waves transmitted respectively in each of the at least three wave transmitting conditions.

12. The method according to claim 11, wherein each of the at least three wave transmitting conditions includes at least one item selected from a group constituting of an acoustic pressure, a voltage of the drive signal to drive said ultrasonic probe, an ultrasonic frequency, a number of ultrasonic waves and a number of drive signals generated per unit time.

13. The method according to claim 11, wherein the at least three wave transmitting conditions include the first wave transmitting condition for acquiring ultrasonic image without destructing the contrast medium, the second wave transmitting condition for destructing the contrast medium and the third wave transmitting condition different from the first and second wave transmitting conditions;

to supply the drive signals, the drive signals are supplied to switch the second wave transmitting condition, the third wave transmitting condition and the first wave transmitting condition; and to generate the ultrasonic image, a plurality of ultrasonic images are generated in real time from the reflection wave obtained from an ultrasonic wave transmitted in the third wave transmitting condition and a plurality of ultrasonic images are generated in real time from the reflection wave obtained from an ultrasonic wave transmitted in the first wave transmitting condition.

14. The method according to claim 11, wherein said supplying the drive signals is carried out in response to respective input commands or automatically at predefined timings.

15. The method according to claim 11, further comprising: displaying a first ultrasonic image and a second ultrasonic image simultaneously, either separated each other or overlapping each other at spatial positions, the first ultrasonic image being obtained from the ultrasonic wave transmitted in the first wave transmitting condition and the second ultrasonic image being obtained from the ultrasonic wave transmitted in the third wave transmitting condition.

16. A memory storing computer-executable program code for controlling an ultrasonic diagnostic apparatus which scans a predetermined region of a subject with a contrast medium injected by using an ultrasonic probe, and which generates an ultrasonic image, said program code comprising:

first means for causing a computer to supply drive signals to said ultrasonic probe to switch at least three wave transmitting conditions in a predetermined order, each of the at least three wave transmitting conditions being for acquiring distribution information on the contrast medium in the tissues of said predetermined region and showing different contrast medium destructing abilities; and second means for causing a computer to generate an ultrasonic image from a reflection wave obtained from at least one of the ultrasonic waves transmitted respectively in each of the at least three wave transmitting conditions.

17. The memory according to claim 16, wherein the at least three wave transmitting conditions include the first wave transmitting condition for acquiring ultrasonic image without destructing the contrast medium, the second wave transmitting condition for destructing the contrast medium and the third wave transmitting condition different from the first and second wave transmitting conditions; said first means supplies the drive signals to said ultrasonic probe generation unit to switch the second wave transmitting condition, the third wave transmitting condition and the first wave transmitting condition; and said second means generates in real time a plurality of ultrasonic images from the reflection wave obtained from an ultrasonic wave transmitted in the third wave transmitting condition and generates in real time a plurality of ultrasonic images from the reflection wave obtained from an ultrasonic wave transmitted in the first wave transmitting condition.

18. The memory according to claim 16, wherein each of the at least three wave transmitting conditions includes at least one item selected from a group consisting of an acoustic pressure, a voltage of the drive signal of said ultrasonic probe, an ultrasonic frequency, a number of ultrasonic waves and a number of drive signals generated per unit time.

19. The memory according to claim 16, wherein said first means supplies the drive signals to said probe according to a first program which define a predetermined sequence of diagnosis to switch the first wave transmitting condition, the second wave transmitting condition and the third wave transmitting condition in a predetermined order, to diagnose blood flow in tissues and the blood flow in a vascular system.

20. The memory according to claim 16, further comprising:

third means for causing a computer to register newly a second program different from the first program;

wherein said first means supplies the drive signals to said probe in accordance with the first program or the second program.

21. The memory according to claim 16, further comprising: said fourth means for causing a computer to display the first ultrasonic image obtained from the ultrasonic wave transmitted in the first wave transmitting conditions and the second ultrasonic image obtained from the ultrasonic wave transmitted in the third wave transmitting conditions simultaneously, either separated each other or overlapping each other at spatial positions.

* * * * *